(12) United States Patent
Moore et al.

(10) Patent No.: US 9,526,442 B2
(45) Date of Patent: Dec. 27, 2016

(54) SYSTEM AND METHOD TO CAPTURE AND PROCESS BODY MEASUREMENTS

(71) Applicant: Fit3D, Inc., Redwood City, CA (US)

(72) Inventors: Gregory A. Moore, San Francisco, CA (US); Tyler H. Carter, Palo Alto, CA (US); Timothy M. Driedger, San Carlos, CA (US)

(73) Assignee: Fit3D, Inc., Redwood City, CA (US)

( * ) Notice: Subject to any disclaimer, the term of this patent is extended or adjusted under 35 U.S.C. 154(b) by 197 days.

(21) Appl. No.: 14/269,134

(22) Filed: May 3, 2014

(65) Prior Publication Data
US 2014/0348417 A1 Nov. 27, 2014

Related U.S. Application Data

(60) Provisional application No. 61/819,482, filed on May 3, 2013.

(51) Int. Cl.
*A61B 5/107* (2006.01)

(52) U.S. Cl.
CPC ........... *A61B 5/1075* (2013.01); *A61B 5/1079* (2013.01)

(58) Field of Classification Search
CPC ............................ A61B 5/1075; A61B 5/1079
See application file for complete search history.

(56) References Cited

U.S. PATENT DOCUMENTS

| | | | | |
|---|---|---|---|---|
| 2004/0083142 A1* | 4/2004 | Kozzinn | ............... | A41H 1/00 705/26.5 |
| 2011/0298897 A1* | 12/2011 | Sareen | ............... | G06N 3/006 348/47 |
| 2011/0306468 A1* | 12/2011 | Wilson | ............... | G06F 19/3475 482/8 |
| 2013/0137942 A1* | 5/2013 | Karo | ............... | A61B 5/0537 600/301 |
| 2013/0261470 A1* | 10/2013 | Allison | ............... | A61B 5/1073 600/476 |

OTHER PUBLICATIONS

Jing Tong, Jin Zhou, Ligang Liu, Zhigeng Pan, and Hao Yan "Scanning 3D Full Human Bodies Using Kinects", Apr. 2012, IEEE Transactions on Visualiation and Computer Graphics, vol. 18, No. 4, pp. 643-650.*

Alexander Weiss, David Hirshburg, and Michael J. Black "Home 3D Body Scans from Noisy Image and Range Data", 2011, In 13th International Conference on Computer Vision.*

* cited by examiner

*Primary Examiner* — Siamak Harandi
(74) *Attorney, Agent, or Firm* — Thorpe North & Western

(57) ABSTRACT

The present invention is directed to system and method capture and process body measurement data including one or more body scanners, each body scanner configured to capture a plurality depth images of a user. A backend system, coupled to each body scanner, is configured to receive the plurality of depth images, generate a three dimensional avatar of the user based on the plurality of depth images, and generate a set of body measurements of the user based on the avatar. A repository is in communication with the backend system and configured to associate the body scanner data with the user and store the body scanner data.

17 Claims, 18 Drawing Sheets

```
While (true) {
        if(handle buttons pressed && state == ready) {
                send "in progress" keystroke signal to computer
                set state: in_progress
                begin slow acceleration to max speed
        }
        if(microcontroller at deceleration position && state == in_progress) {
                begin deceleration to stop
        }
        if(microcontroller at end position && state == in_progress) {
                send "success" keystroke signal to computer
                set state: successful
                stop turntable
        }
        if(handle buttons released && state == in_progress) {
                send "failed" keystroke signal to computer
                set state: failed
                stop turntable
        }
        if(calibration button pressed && state != in_progress) {
                set state: calibration
                start turntable
        }
        if(state == calibration && microcontroller at start position) {
                set state: ready
                stop turntable
        }
}
```

FIGURE 6

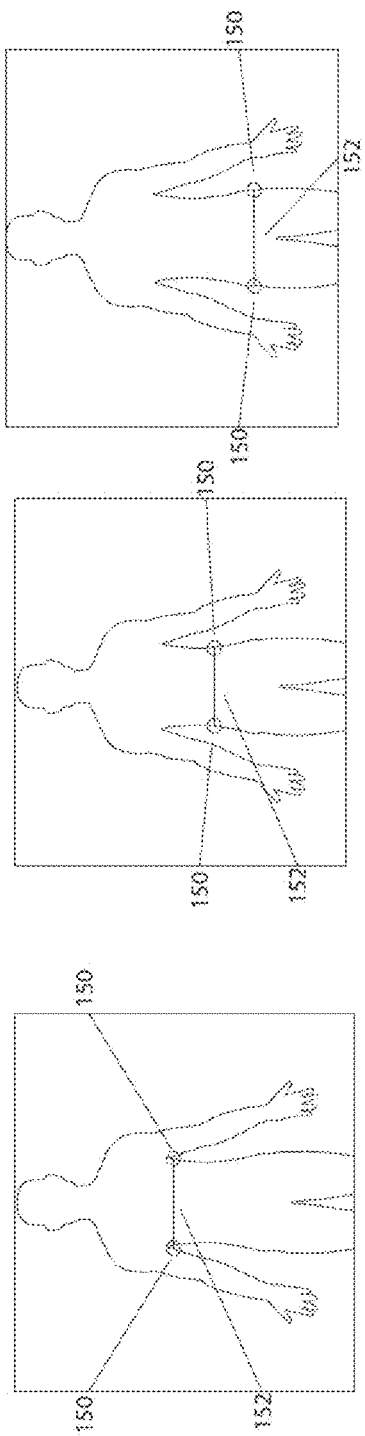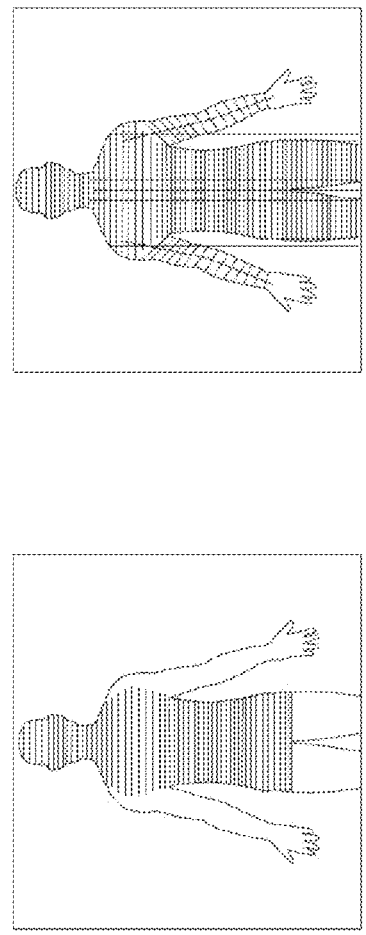
FIGURE 17a
FIGURE 17b
FIGURE 17c
FIGURE 17d
FIGURE 17e

SYSTEM AND METHOD TO CAPTURE AND PROCESS BODY MEASUREMENTS

FIELD OF THE INVENTION

The disclosure relates generally to a health system and in particular to a system and method for capturing and processing body measurements.

BACKGROUND

Current systems lack the ability to capture to-scale human body avatars, extract precise body measurements, and securely store and aggregate and process that data for the purpose of data dissemination over on the Internet. In the past, if a person wanted to capture body measurements, he or she would have to either wrap a tape measure around his or her body parts, write down those measurements, and then find a way to store and track those measurements. A person would do this to get fitted for clothing, assess his or her health based on their body measurements, track his or her body measurement changes over time, or some other application that used his or her measurements. This process is very error prone, is not precisely repeatable, and these measurements are not stored on connected servers where the information is accessible and the user cannot track his or her changes. In addition, there is no system that can capture these body measurements and then generate a to-scale human body avatar.

There are a number of existing body scanning systems. For example, TC-2 (NX-16 and KX-16), Vitus (Smart XXL), Styku (MeasureMe), BodyMetrics and Me-Ality are examples of these existing body scanning systems. Each of these systems is a body scanner where the user stands still in a spread pose and the system then create body contour maps based on depth sensors, white light projectors and cameras, or lasers. These systems then use those body contour maps (avatars) to extract measurements about the user. In each case, the body scanners is used to extract measurements for the purposes of clothing fitting or to create an avatar that the user can play with. Each of these known systems is extremely complicated expensive and therefore cannot be distributed widely to the mainstream markets. Furthermore, none of the aforementioned systems offer an online storage facility for the data captured and users can simply use the measurements at the store that houses the scanner. Another missing component in these systems is data aggregation from each of these scanning systems.

There are also a number of existing companies that allow users to enter body measurement data online. These companies include healthehuman, weightbydate, trackmybody, Visual Fitness Planner, Fitbit, and Withings and all of these companies allow users to manually enter their body measurements using their online platforms. These companies are mainly focused on the following girth measurements because they are easily accessible: neck, shoulders, chest, waist, hips, left and right biceps, elbows, forearms, wrists, thighs, knees, calves, and ankles. These systems allow the user to track these measurements over time. These companies do not solve the problem because user measurements are extremely subjective, therefore accuracy cannot be determined, user measurements are not repeatable, and therefore cannot be used to form trends. Furthermore, users that have hundreds of additional measurements cannot be manually captured and therefore are not included in the aforementioned company's trend analysis. Also, average users that have extremely short attention spans generally do not want to capture measurement with a tape measure and then input those measurements into an application. This process is time consuming and error prone. Therefore time is a large problem for the current sets of solutions.

SUMMARY

The present invention is directed to system and method capture and process body measurement data including one or more body scanners, each body scanner configured to capture a plurality depth images of a user. A backend system, coupled to each body scanner, is configured to receive the plurality of depth images, generate a three dimensional avatar of the user based on the plurality of depth images, and generate a set of body measurements of the user based on the avatar. A repository is in communication with the backend system and configured to associate the body scanner data with the user and store the body scanner data.

These and other features, aspects, and advantages of the invention will become better understood with reference to the following description, appended claims, and accompanying drawings.

BRIEF DESCRIPTION OF THE DRAWINGS

FIG. 6 is an example of pseudocode operating on the scanning device;

FIGS. 17a-17e illustrate an example of a landmarks and visual indicia of body measurements generated by the system.

DETAILED DESCRIPTION

The disclosure is particularly applicable to systems that capture body scans, create avatars from the body scan, extract body measurements, and securely aggregate and display motivating visualizations and data. It is in this context that the disclosure will be described. It will be appreciated, however, that the system and method has greater utility since it can also be implemented as a standalone system and with other computer system architectures that are within the scope of the disclosure.

Figure 1:
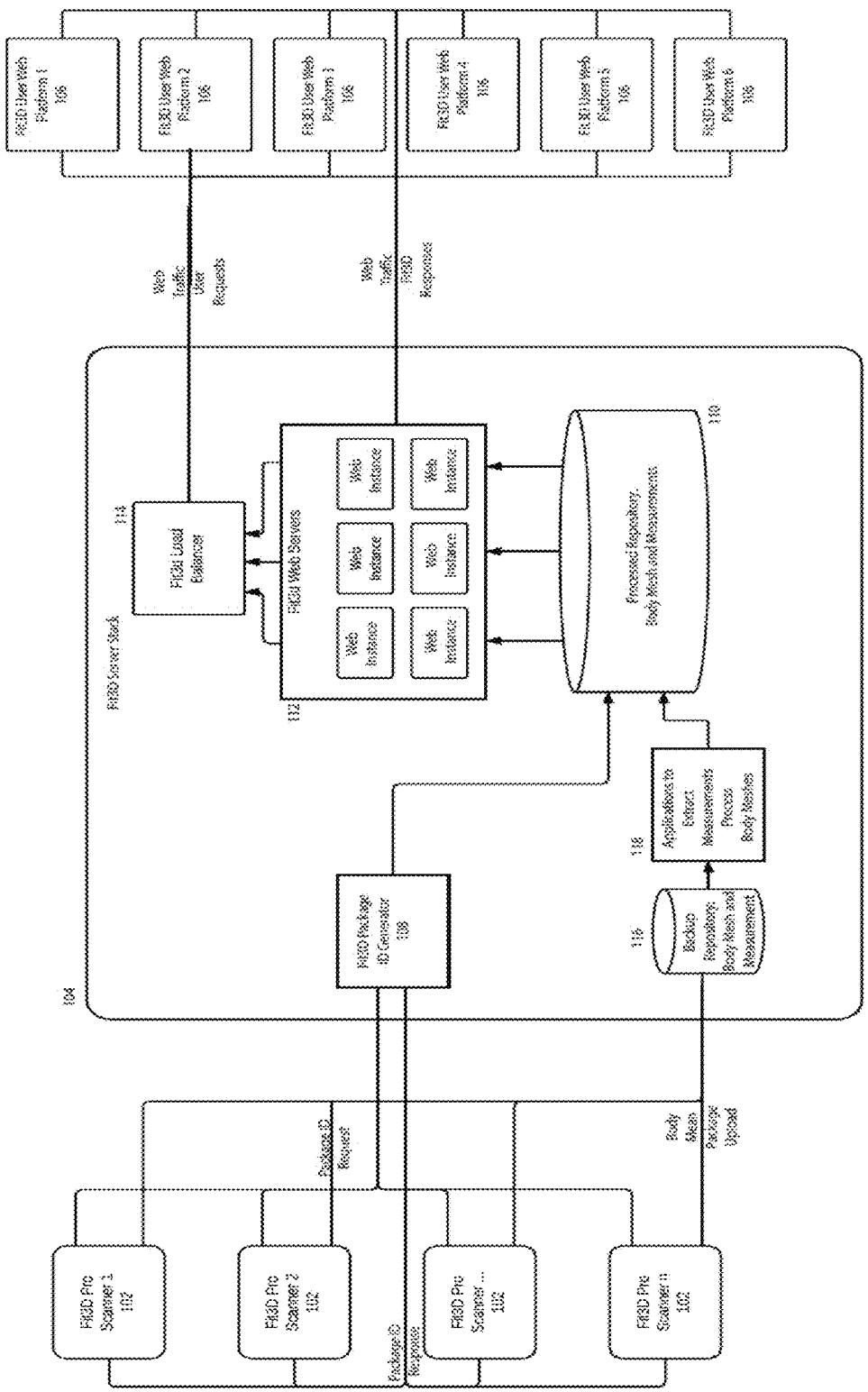
FIG. 1 illustrates a body measure capture and processing system.

FIG. 1 illustrates a body measurement capture and processing system. The body measurement capture and processing system may include one or more scanners 102, such as scanners $102_1$ to $102_n$ as shown in FIG. 1, that are each coupled to a backend system 104 which may be coupled to one or more user computing devices 106, such as computing devices $106_1$ to $106_n$ as shown in FIG. 1, wherein each user computing device may allow the user to interact with a web platform of the user. Each of these components may be coupled to each other over a communication path that may be a wired or wireless communication path, such as a web, the Internet, a wireless data network, a computer network, an Ethernet network, a cellular telephone network, a telephone network, Bluetooth and the like. In operation, the one or more scanners 102 may be used to scan a body of a user of the system, such as a person or animal, and form a body mesh that is transferred to the backend system 104 that processes and stores the body mesh and generates the avatar of the user which is then displayed to the user in the web or other platform for the user along with various body measurements of the user.

Each scanner 102 may be implemented using a combination of hardware and software and will be described in more detail below with reference to FIGS. 3-6. In the embodiment shown in FIGS. 3-6, a user is rotated using a turntable 302 past one or more stationary cameras 306 to capture the body mesh of the user. In an alternate embodiment, the user may be stationary and one or more cameras 306 may rotate about the user to capture the body mesh of the user. Each scanner 102 may generate a body mesh of a user (from which an avatar may be created) and then the backend system 104 may assign an identifier to each body mesh package of each user.

An exemplary user computing device 106 may be a computing system that has at least one processor, memory, a display and circuitry operable to communicate with the backend system 104. For example, each user computing device 106 may be a personal computer, a smartphone device, a tablet computer, a terminal and any other device that can couple to the backend system 104 and interact with the backend system 104. In one embodiment, each user computing device 106 may store a local or browser application that is executed by the processor of the user computing device 106 and then enable display of the web platform or application data for the particular user generated by the backend system 104. Each user computing device 106 and the backend system 104 may interact with each user computing device sending requests to the backend system and the backend system sending responses back to the user computing device. For example, the backend system 104 may generate and send an avatar of the user and body measurements of the user to the user computing device that may be displayed in the user's web platform. The web platform of the user may also display other data to the user and allow the user to request various types of information and data from the backend system 104.

The backend system 104 may comprise an ID generator 108 that generates the identifier for the body mesh package of each user, which aids in anonymous and secure information transfer between the backend system and the computing devices. The backend system 104 also may comprise a repository 110 for processed data (including a body mesh for each user and body measurements of each user that may be indexed by the identifier of the body mesh generated above) and one or more web servers 112 (with one or more web instances) that may be used to interact with the web platform of the users. The backend system 104 may also have a load balancer 114 that balances the requests from the user web platforms in a well-known manner. The backend system 104 may also have a backup repository 116 (including a body mesh for each user and body measurements of each user that may be indexed by the identifier of the body mesh generated above) and one or more applications 118 that may be used to extract body measurements from the body mesh and process the body meshes. In one implementation, the backend system 104 may be built using a combination of hardware and software and the software may use Java and MySQL, PostgreSQL, SQLite, Microsoft SQL Server, Oracle, dBASE, flat text, or other known formats for the repositories 110, 116. In one implementation, the hardware of the backend system 104 may be the Amazon Cloud Computing stack that allows for ease of scale of the system as the system has more scanners 102 and additional users.

Figure 2:
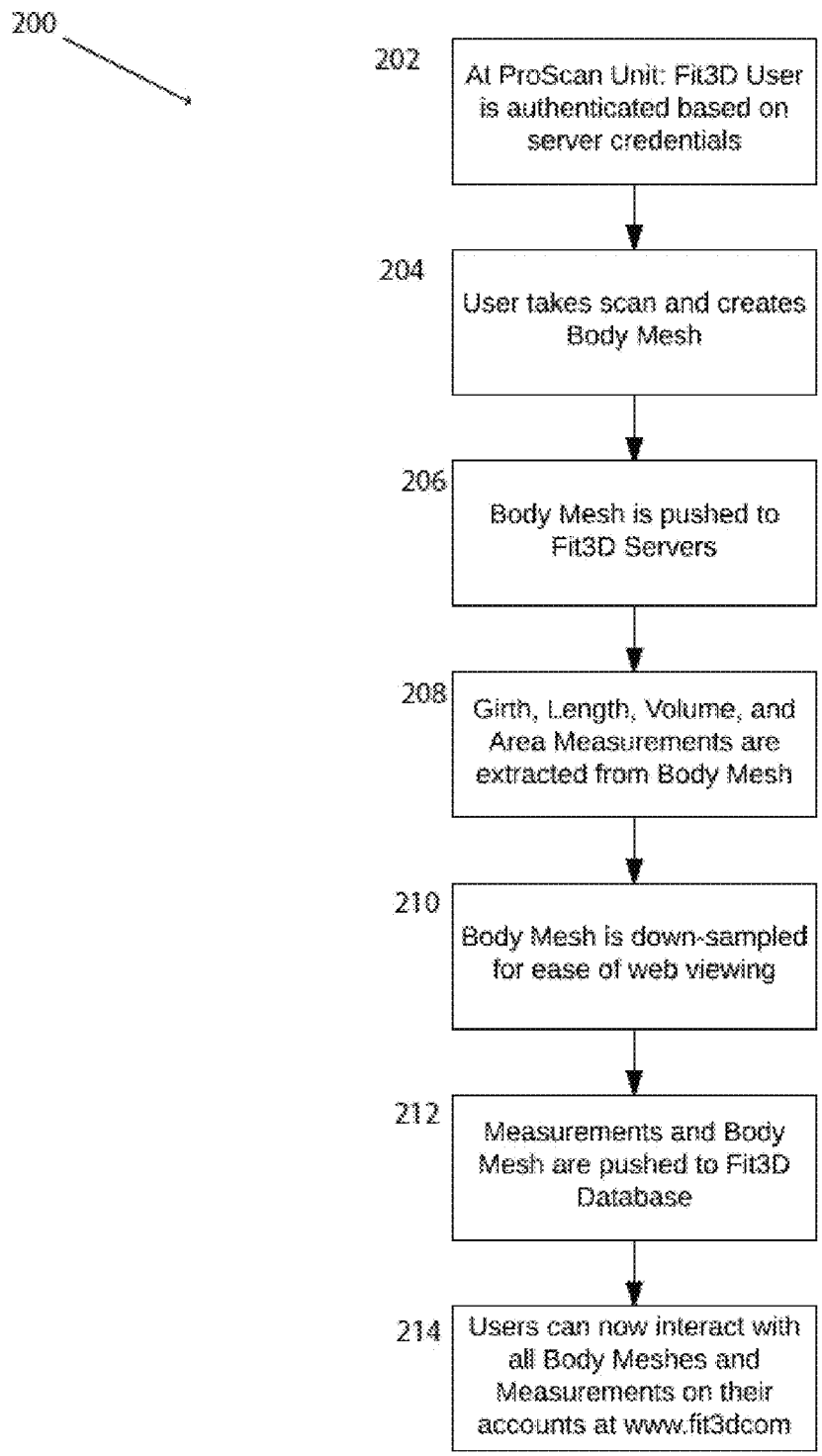
FIG. 2 illustrates a method for capturing body avatars using the system in FIG. 1.

FIG. 2 illustrates a method 200 for capturing body avatars using the system in FIG. 1. The processes described below may be carried out by a combination of the components in FIG. 1 and may be performed in hardware or software or a combination of hardware and software. In the method, a user may, at a scanner 202, may be authenticated by the scanner based on a set of server credentials and then the user may use the scanner to do a body scan 204 and the scanner creates a body mesh. The scanner 202 may then send the body mesh of the user to the backend system 104 (206). One or more body measurements (such as a girth, length, volume and area, including surface, measurements) of the user are extracted from the body mesh (208). The extraction of the body measurements from the body mesh may be performed at the scanner 102 or in the backend system 104. The body mesh may then be down-sampled from ease of web viewing (210). As above, the down-sampling may be performed at the scanner 102 or in the backend system 104. The body measurements and the body mesh for the user may then be stored into the repository 110 (212.) The user of the body mesh and the body measurements may then interact with the avatar (a visual representation of the body mesh), the body measurement, and the body mesh (214) using the web platform session of the user. The user interaction with the avatar, the body measurement and the body mesh may be used for measurement tracking, projections, body morphing, cross-sectional body segment displays, or motivation of the user about health issues.

Figure 3:
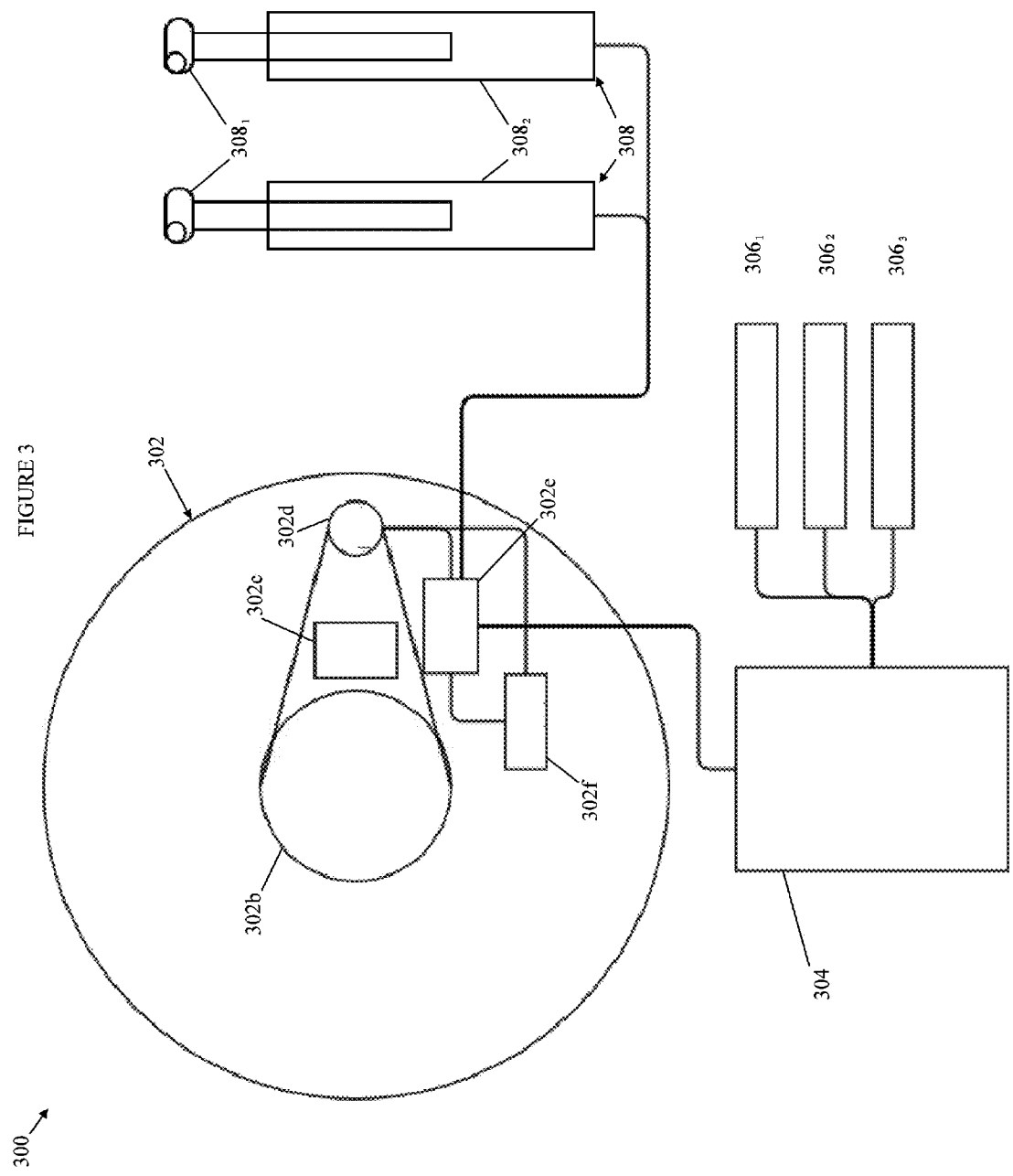
FIG. 3 illustrates an embodiment of a scanning device of the system in FIG. 1.

FIG. 3 illustrates an embodiment of a scanning device of the system in FIG. 1 in which the scanning device has a rotation and scanning mechanism 300 (shown in FIG. 3) that rotates a user during a body scan. The rotation and scanning mechanism 300 may include a rotation device 302, a computing device 304 that is coupled to the rotation device 302, one or more cameras 306 coupled to the computing device 304 for taking images of the body of the user and one or more handles 308.

The rotation device 302 may further include a platform 302a in which a user may stand while the body scan is being performed and a drive gear 302b that causes the platform 302a to rotate under control of other circuits and devices of the rotation device. The rotation device may have a microswitch 302c, a drive motor 302d and a microprocessor 302e that are coupled together and the microprocessor controls the drive motor 302d to control the rotation of the drive gear and thus the rotation of the platform 302a. The microswitch is a sensor that detects the rotation of the platform 302a which may be fed back to the microprocessor and may also be used to trigger the one or more cameras. The rotation device 302 may also have a power supply 302f that supplies power to each of the components of the rotation device.

The microprocessor 302e of the rotation device 302 may be coupled to the computing device 304 that may be a desktop computer, personal computer, a server computer, mobile tablet computer, or mobile smart phone with sufficient processing power and the like that has the ability to control the rotation device 302 through the microprocessor 302e and capture the frames (images or video) from the one or more cameras 306. The computing device 304 may also have software and controls the other elements of the system. For example, FIG. 6 is an example of pseudocode operating on the scanning device. The software may be built using C++, REST Web Communication Protocol, Java or other platforms, languages, or protocols known in the art. The one or more cameras 306, such as cameras $306_1$, $306_2$ and $306_3$ in the example in FIG. 3, may each be a depth sensing and read green blue (RGB) camera. For example, each camera may be a Microsoft Kinect, Asus Xtion Pro or Asus Xtion Pro Live, Primesense Carmine, or any other depth sensing camera which includes any of the following technologies IR emitter and IR receiver, color receiver. As shown in FIG. 3, the one or more handles 308 may be coupled to and controlled by the microprocessor 302e. Each handle 308 may have adjustable height and further have an upper portion $308_1$ on which a user may grasp during the body scan and a base portion $308_2$ into which the upper portion $308_1$ may slide to adjust the position of the handle to accommodate different users.

Figure 5:
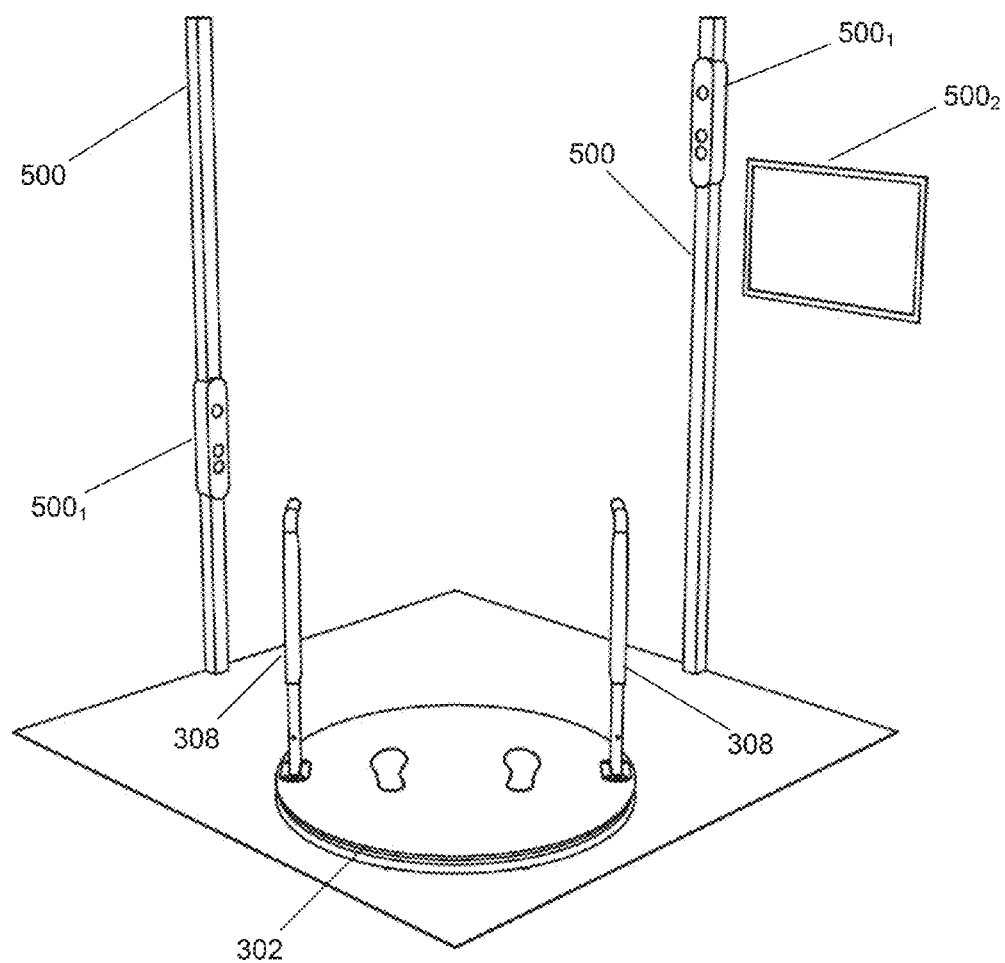
FIG. 5 illustrates an example of an embodiment of the scanning device in FIG. 3.

FIG. 5 illustrates an example of an embodiment of the scanning device in FIG. 3 with the handles 308, the rotation device 302. In this embodiment, the one or more cameras may be mounted on standards 500 that have a camera bay $500_1$, illustrated at different heights, into which each camera is mounted. The camera bay on each standard may be vertically adjusted to adjust the height of each camera to accommodate different users. Furthermore, the cameras may also be at different heights from each other as shown in FIG. 5 to capture the entire body of the user. In the embodiment shown in FIG. 5, a display $500_2$ of the computing device may be attached to a wall near the body scanner.

Figure 7:
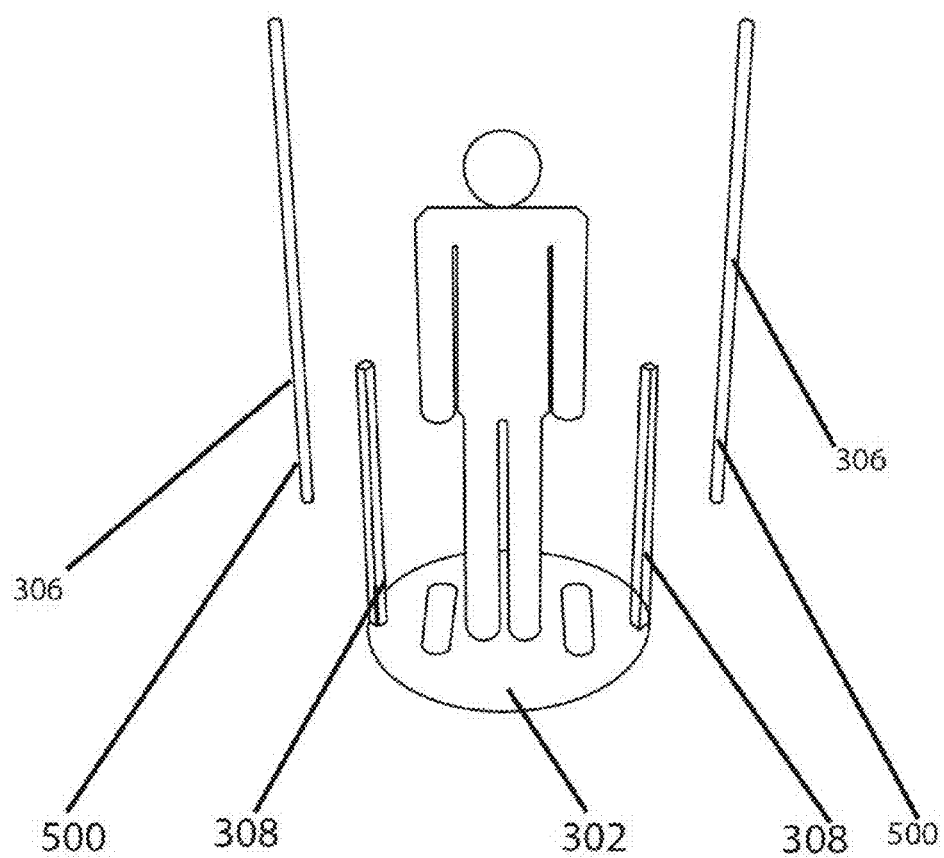
FIG. 7 illustrates a user on the scanning device.
Figure 8:
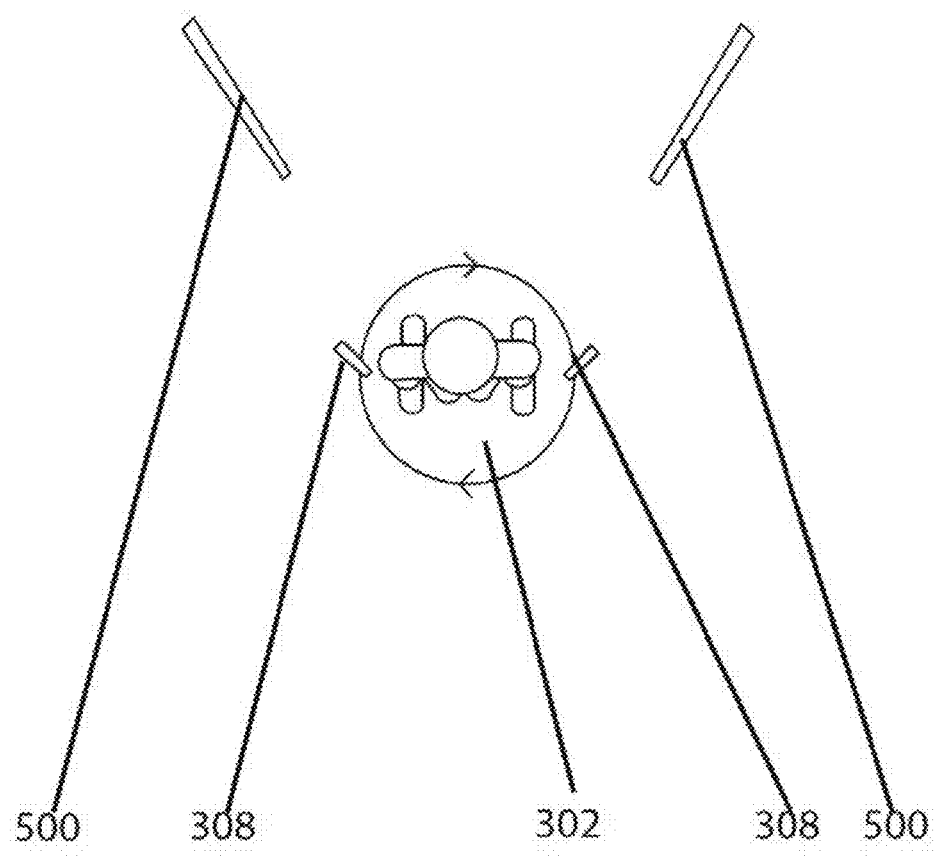
FIG. 8 illustrates the embodiment of the scanning device in which the user is rotated past stationary cameras.
Figure 9:
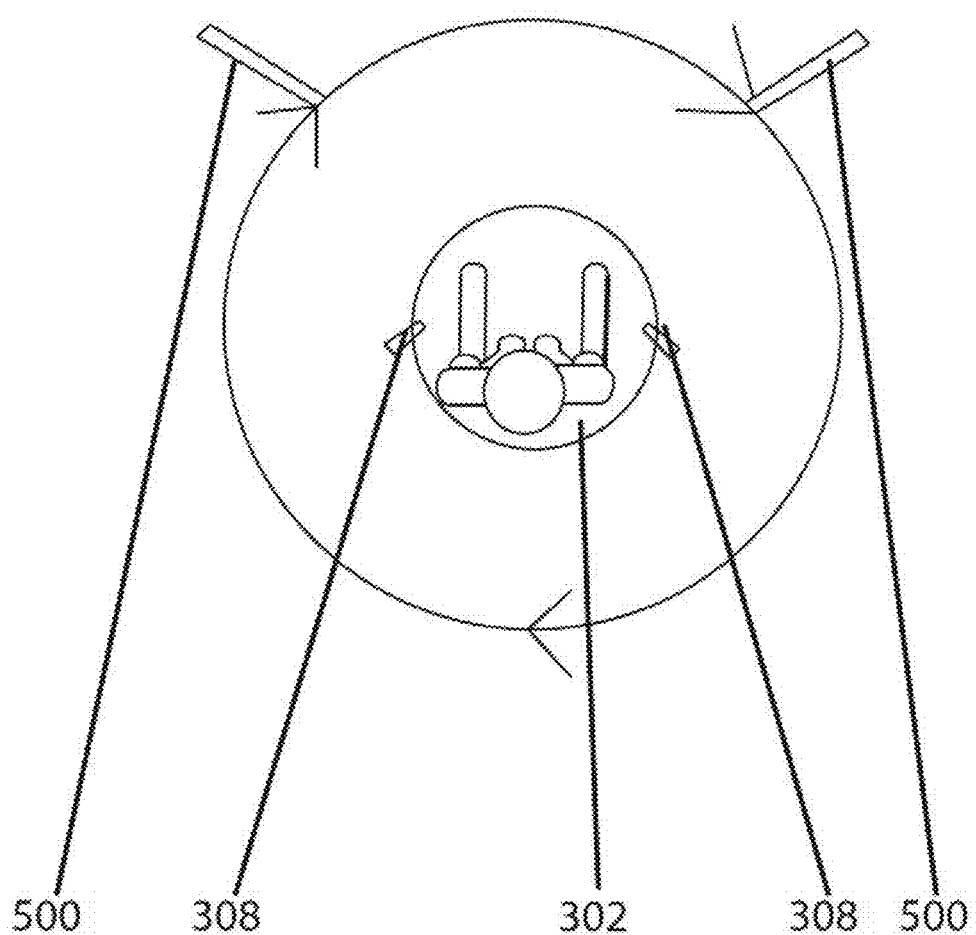
FIG. 9 illustrates the embodiment of the scanning device in which the user is stationary and the cameras are moving.

FIG. 7 illustrates a user on the platform 302 of the scanning device that has the handles 308 and standards 500 that mounts the one or more cameras. FIG. 8 illustrates the embodiment of the scanning device in which the user on the platform 302 is rotated past stationary cameras that is mounted on the standards 500. FIG. 9 illustrates the embodiment of the scanning device in which the user is stationary on the platform 302 and the standards 500 with the one or more cameras are moving relative to the user.

FIGS. 18a-18e illustrate an example sequence of captured depth images of a user. In one configuration a single camera 306 is employed during rotation. The camera 306 captures images at various heights and from various relative user positions.

Figure 4:
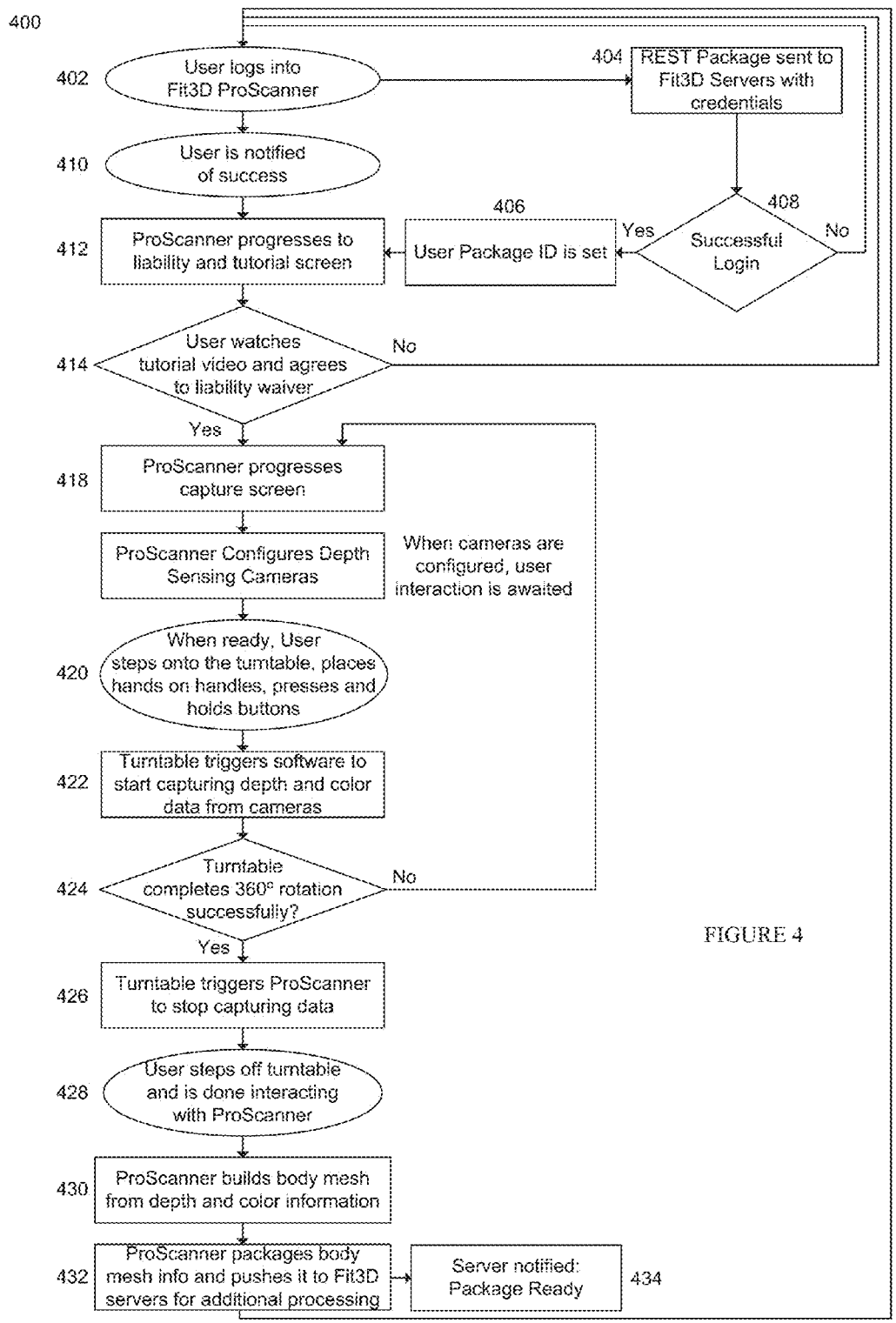
FIG. 4 illustrates a method for operating the scanning device in FIG. 3.

FIG. 4 illustrates a method 400 for operating the scanning device in FIG. 3. The method shown in FIG. 4 may be carried out by the various hardware and software components of the rotation and scanning mechanism 300 in FIG. 3. In the method, the user logs into a body scanner (402) and an authentication package (that may be done using, for example, the REST protocol) is sent to the backend system in FIG. 1 with credentials (404.) If the login is not successful (408), the method loops back to the user login. If the login is successful, a user body mesh package identifier is set (406) that is used to identify the body scan of the user in the system and the user is notified of the successful login (410.) The computing device of the scanning device may have a display and may display several user interface screens (412), display a welcome tutorial and agrees to a liability waiver (414.) If the user does not agree to the liability waiver, then the user is logged out.

Once the user accepts the liability waiver, the computing device may display an image capture screen (416) and the one or more cameras are configured (418.) The user may then step onto the platform (420) and the user may grab onto the handles. The platform begins to rotate and the one or more cameras begin to capture body scan data (422). The software in the computing device and the microprocessor tracks the rotation of the platform and detects if the platform has rotated 360 degrees or more (424). If at least 360 degree rotation has been completed, then the microswitch, or additional internal software triggering as a result of a timer based from the microswitch, may trigger the cameras to stop capturing data (426.) The user may then step off the platform (428.) Software in the computing device 304 of the scanner may then generate a body mesh from the data from the one or more cameras, or the software may generate a body mesh as the cameras are actively capturing body scan data (430.) Software in the computing device 304 of the scanner may then package the body mesh data of the user into a package that may be identified by the identifier and the package may be sent to the backend system 104 (432, 434.)

Referring to FIGS. 17a-17e, in the backend system 104, the computing resources may execute a plurality of lines of computer code that generate body measurements based on the body scan based on landmarks 150 on the body. The system locates desired landmarks 150 on the body, via such methods as silhouette analysis, which projects three-dimensional body scanned data onto a two-dimensional surface and observes the variations in curvature and depth, minimum circumference, which uses the variations of the circumference of body parts to define the locations of the landmarks 150 and feature lines, gray-scale detection, which converts the color information of human body from RGB values into gray-scale values to locate the landmarks 150 with greater variations in brightness, or human-body contour plot, which simulates the sense of touch to locate landmarks 150 by finding the prominent and concave parts on the human body. Additional non-limiting disclosure of landmark 150 location processing is in U.S. Pat. App. No. 20060171590 to Lu et al, which is hereby incorporated by reference. The system locates selected landmarks and measures a distance between them and correlates the distance to a body measurement 152. Representative landmarks include the feet (bottom, arch), the calf (front, rear, sides), thigh (front, rear, sides), torso, waist, chest, neck (front, rear, sides), head (crown, sides). In exemplary configuration, the images, mesh, landmarks, and the body measurements 152 are stored in the repository 110. It should be noted that for visual clarity, body measurement 152 reference numbers are not included. In further exemplary configuration, the data is associated with the user identifier and time/date information.

Figure 16:
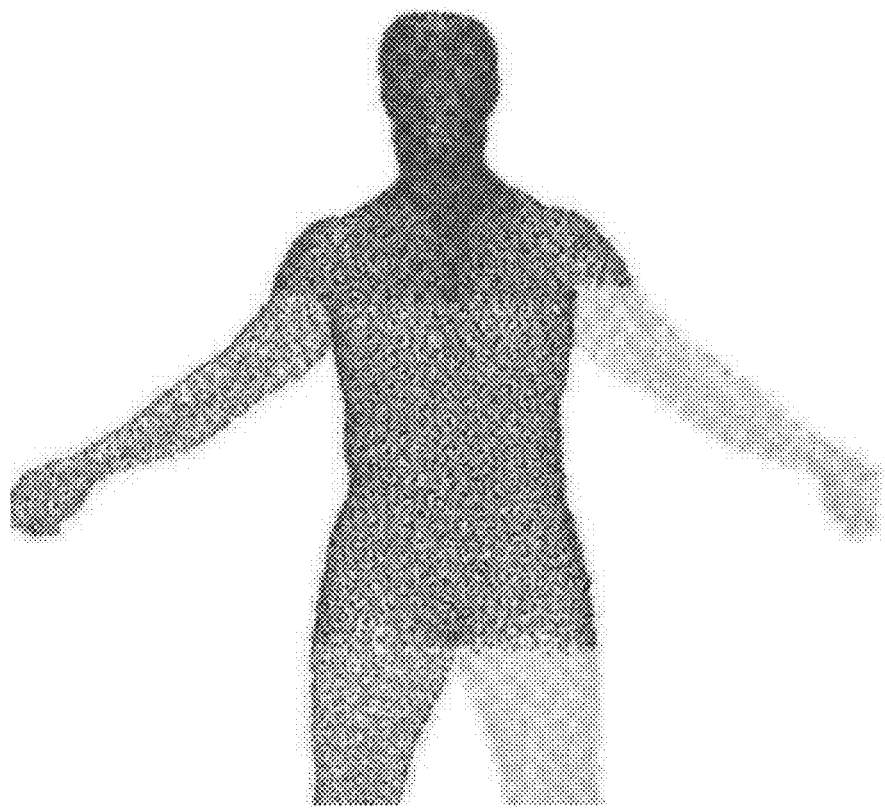
FIG. 16 illustrates an example partial body mesh generated by the system.
Figure 18C:
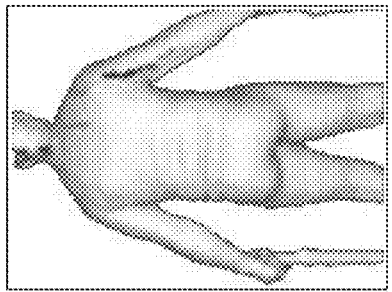
FIGS. 18a-18e illustrate an example sequence of captured depth images of a user.
Figure 18B:
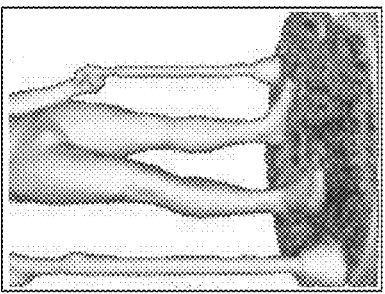
Figure 18A:
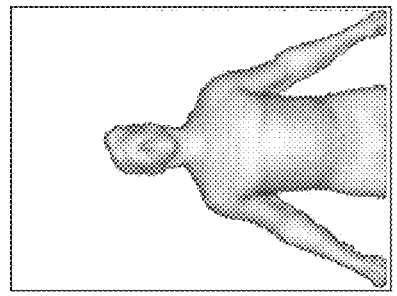
Figure 18E:
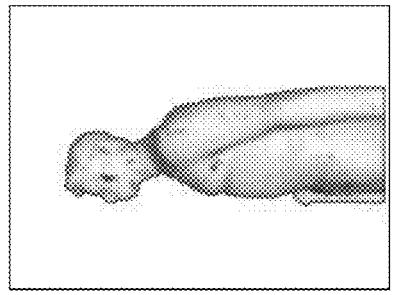
Figure 18D:
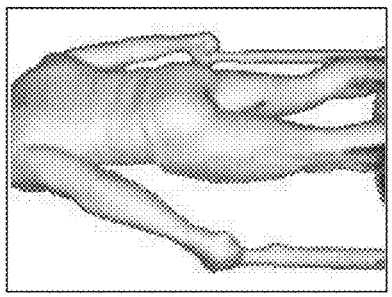

In one implementation, the system may use a measurement extraction algorithm and application from a company called [TC]2. The backend system 104, using the [TC]2 application or another method, may extract multiple girth and length measurements as well as body and segment volumes and body and segment surface areas. For example, 150 body measurements or more may be extracted, as shown in the representative measures of FIG. 16.

Figure 10:
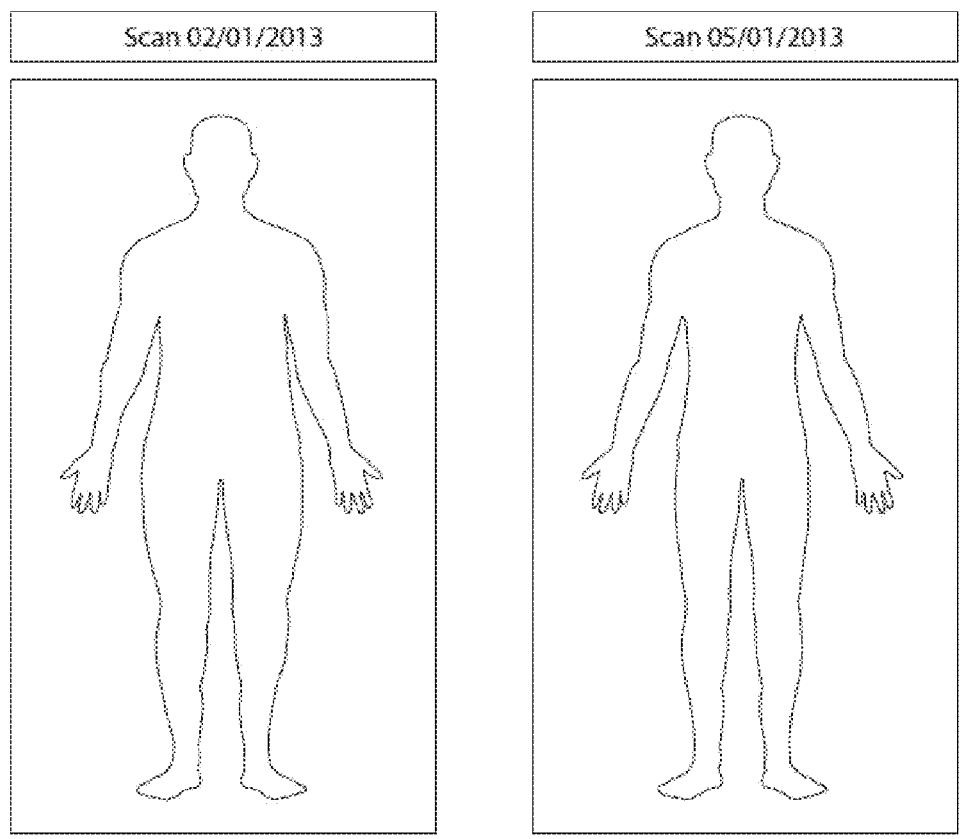
FIG. 10 illustrates an example of a user interface screen of the web platform for a user showing a comparison between body avatars over time.
Figure 12:
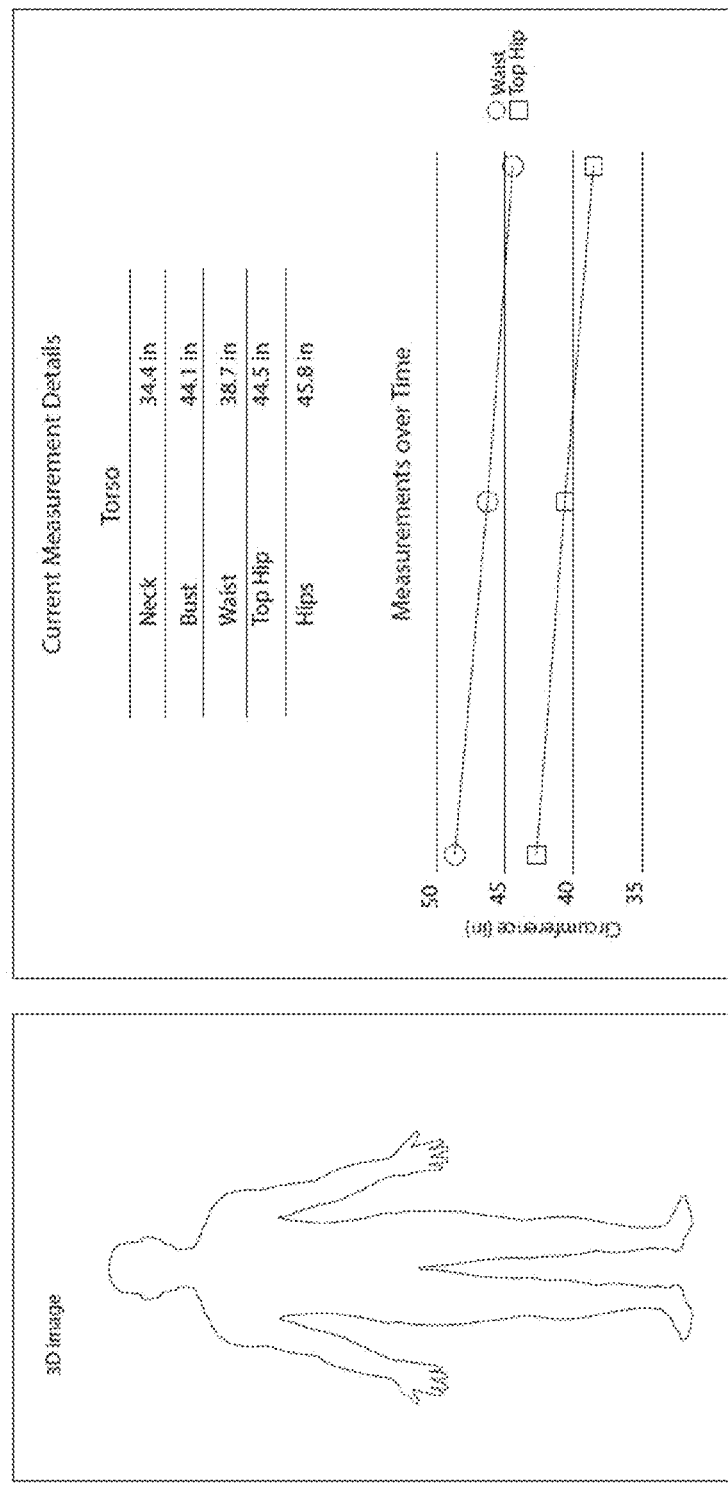
FIG. 12 illustrates an example of a user interface screen of the web platform for a user showing body measurement tracking.
Figure 13:
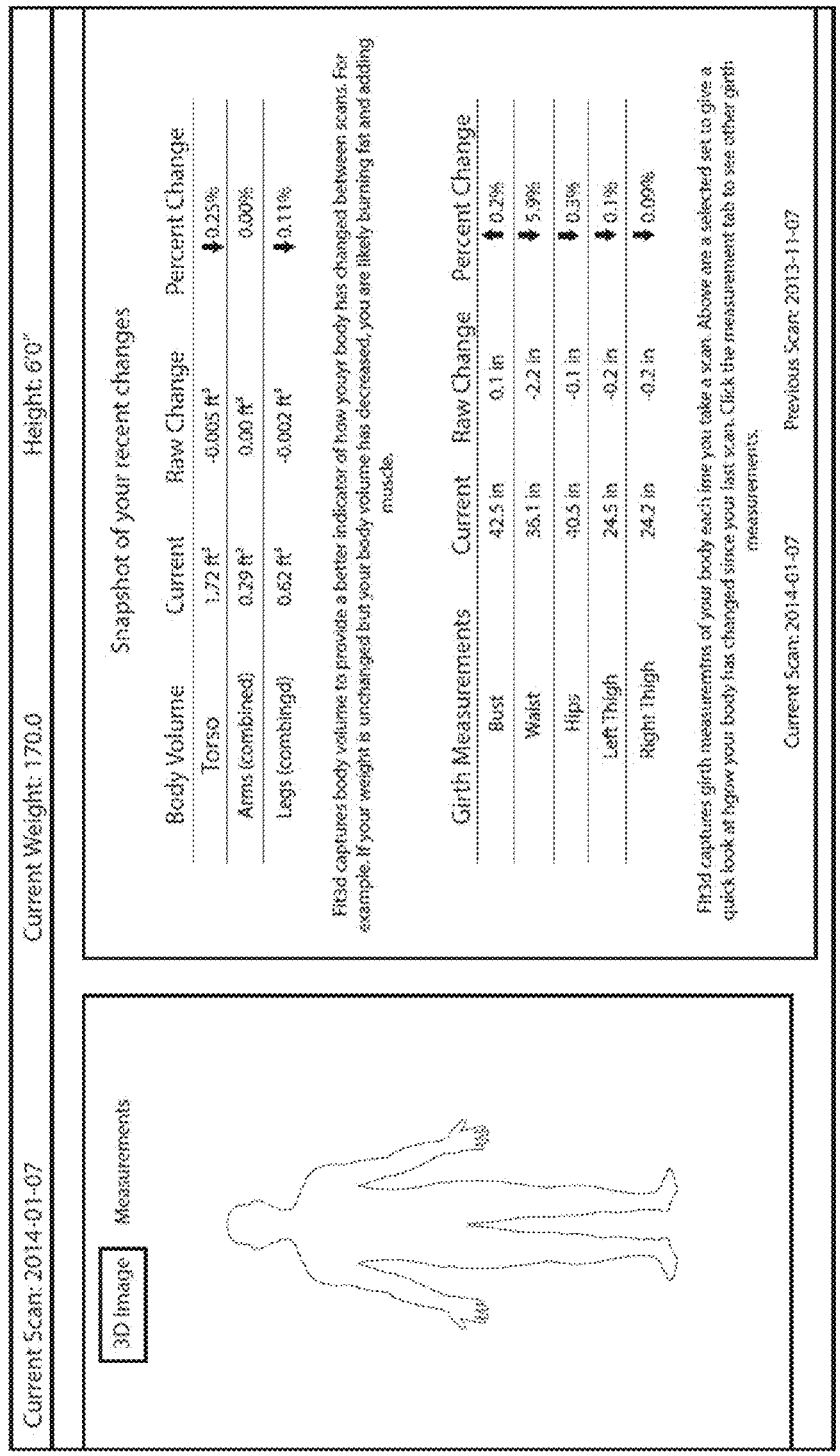
FIG. 13 illustrates an example of a user interface screen of the web platform for a user showing an assessment of the user.

FIGS. 10, 12, and 13 illustrate body scan data associated with a user from a first body scan time and a second, different body scan time. As an example, the system may be used by a user to track weight loss progress. Specifically, a user can utilize the system to track their progress with any fitness and/or nutrition program or just track their body as it changes throughout their life. The system may have installed body scanners 102 in fitness facilities, personal training facilities, weight loss clinics, and other areas where mass numbers of people traffic. The user will be able login to any of the body scanners 102 with authenticating information and capture a scan of their body. This scan may be uploaded to the backend system 104 where measurements will be extracted, their scan will be processed for viewing on the web and stored. The user can then in a web platform 106 using a computing device pull up a recent personal avatar and measurements and/or a history of their avatars and measurements. The user can then use the system to see how specific areas of their body are changing, for example, if a user's biceps are growing in size, but his or her waist is shrinking, the user will be able to see this by way of raw measurement data as well as by comparing their timeline of avatars through the system.

Figure 11:
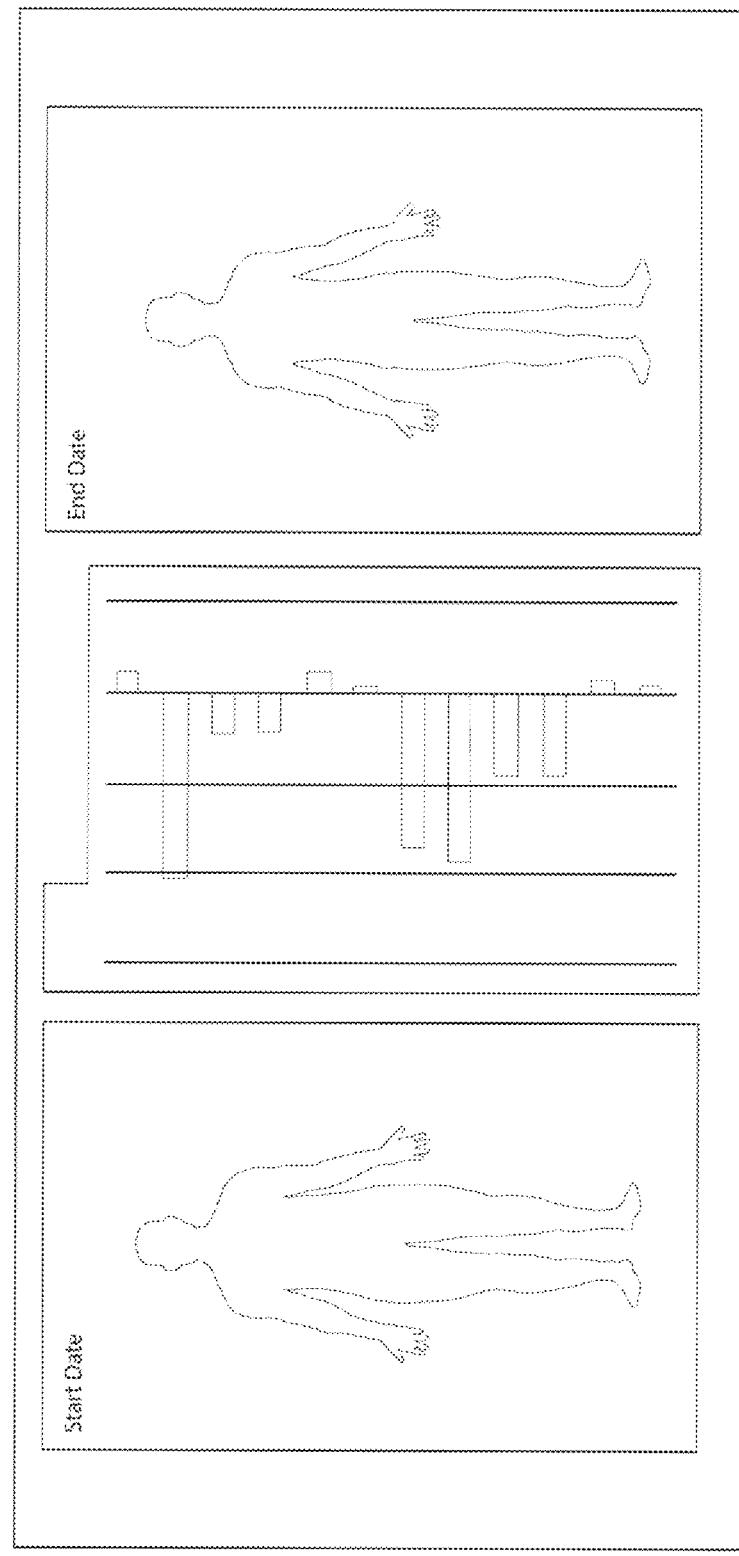
FIG. 11 illustrates an example of a user interface screen of the web platform for a user showing projected results.
Figure 14:
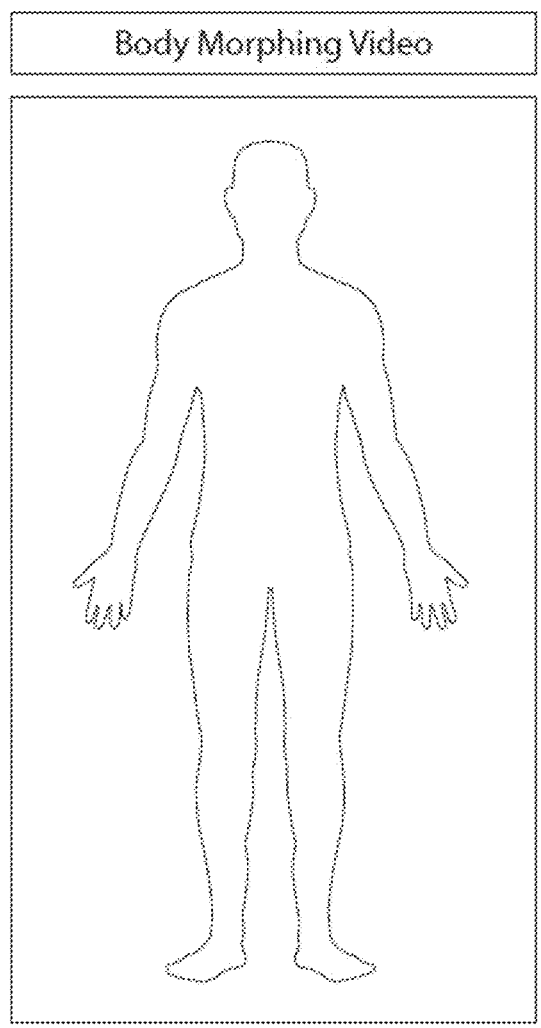
FIG. 14 illustrates an example of a user interface screen of the web platform for a user that has a body morphing video that the user can view.
Figure 15:
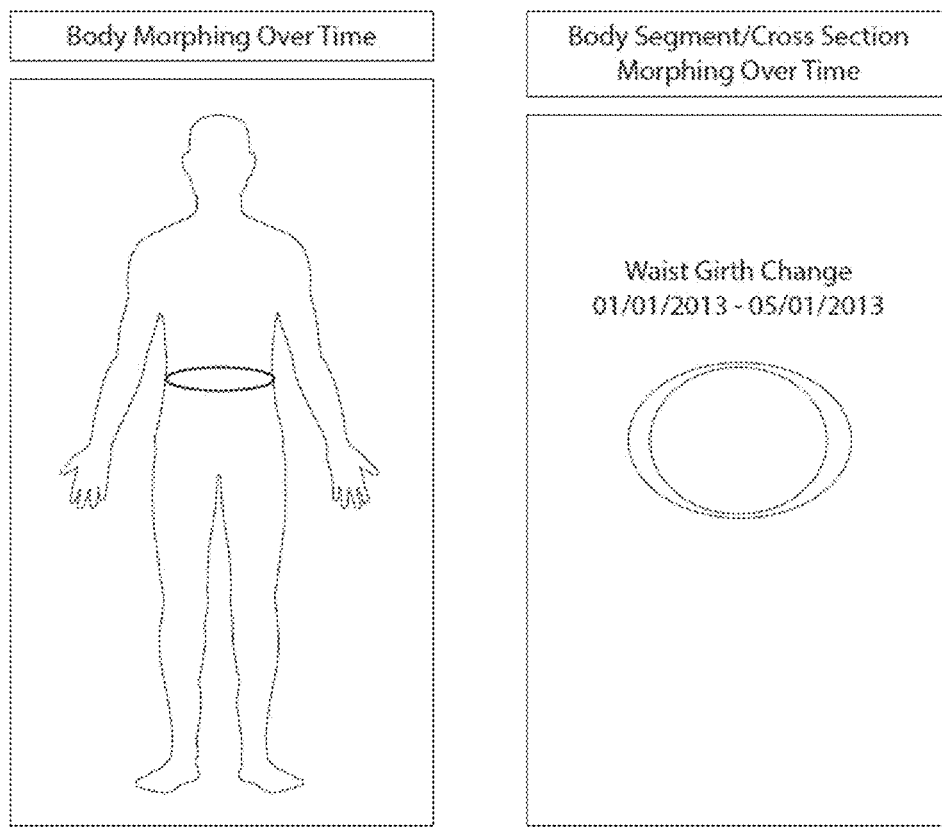
FIG. 15 illustrates an example of a user interface screen of the web platform for a user that has a body cross sectional change.

FIGS. 11, 14, and 15 illustrate an interface with user body scan data from a selected time and a projected body avatar. As another example, a user can use the system to project future body shape and measurements. Since the system is aggregating a unique set of measurements that has never before been aggregated, the system can perform projective analytics. For example, there are thousands of body types in the world and each of these body types have limitations to the amount of weight or girth that they can gain or shed. The system has the unique opportunity to categorize body types based on objective measurement data as opposed to the industry standard, which is apple, pear, or square shaped bodies. The system may also aggregate nationality, demographic, biometric measurements, third party activity and caloric intake data, and others and are building reference body change trajectories based on that data. These body type categories are based on several ratios that are captured and compared to the larger set of data. These ratios may include, but are not limited to, all combinations of ratios between, among, or actual values of the following body parts: neck girth, upper arm girth, elbow girth, forearm girth, wrist girth, chest girth, waist girth, hip girth, thigh girth, knee girth, calf girth, ankle girth, segmental body surface area, length, and/or volume. By taking into account the girths, volumes, lengths, and areas of a body, the system can define limitations in body growth or shrinkage based on the entirety of the set of community data. For example if a man who is 18 years old takes a scan and it is found that this person's waist to hip ratio is above a certain amount and his thigh to waist ratio is less than some certain amount, it is highly unlikely that this person will be able to look like many of the fitness models. This being said, the system can utilize the data pool that the system has captured to assess project a set of body measurement goals based on his nutrition (caloric intake) and activity (including type of activity) what his measurements may be in the future. By assessing the entire set of data, the system can better predict and project the realistic goals of each individual user.

The system may then be used for men and women that want to gain or lose girth and weight. For example, a very skinny man comes into a training facility and mentions to the training staff that he wants to put on 20 pounds of muscle in 1 year. The staff, knowing that this is highly improbable if not impossible may try to quell this man's expectations, sell their services by lying, or pass on the opportunity to train this person because their goals cannot be achieved. However, using the system, the staff can take a scan of the man using the body scanner 102 and enter additional data into the system. The operators of the body scanner 102 may then use the system's projection tools and, with the addition of generic nutrition information like average protein and carbohydrate caloric intake and generic exercise activity types and levels, can project what this man's avatar and measurements may be in a month, quarter, year, or several years based on the amassed data and resultant analytics generated by the backend system 104. Thus, the training facility has the tools to set a user's expectations based on objective and quantitative data, has the ability to design a plan to get that user on his path to success, and has the ability to capture additional scans along the way so that the trainer and user can track the user's progress and make adjustments to the program based on actual data if necessary.

FIG. 10 illustrates an example of a user interface screen of the web platform for a user showing a comparison between body avatars over time. The user interface screen allows the user to see the difference in their generated body avatar generated by the system over time. FIG. 11 illustrates an example of a user interface screen of the web platform for a user showing projected results of a user based on a fitness and nutritional plan and a project body scan of the user if the projected results are achieved. FIG. 12 illustrates an example of a user interface screen of the web platform for a user showing body measurement tracking in which one or more body measurement values are shown. This user interface may also generate a chart (see bottom portion of FIG. 12) that shows one or more body measurements over time. FIG. 13 illustrates an example of a user interface screen of the web platform for a user showing an assessment of the user including one or more values determined, such as waist to hip ratio, body mass index (BMI), etc, by the system. This user interface may also generate a chart (see bottom portion in FIG. 13) that shows one or more assessment values over time.

FIG. 14 illustrates an example of a user interface screen of the web platform for a user that has a body morphing video that the user can view. The body morphing video may start with a first body scan and then morph into the second body scan of the user so that the user can see the changes to their body. FIG. 15 illustrates an example of a user interface screen of the web platform for a user that has a body cross sectional change. In the example in FIG. 15, the user interface may show a cross sectional change over time of waist measurements. Thus, the system may also be used to generate segmental or cross section changes as well, not just the entire body change over time.

While the foregoing has been with reference to a particular embodiment of the invention, it will be appreciated by those skilled in the art that changes in this embodiment may be made without departing from the principles and spirit of the disclosure, the scope of which is defined by the appended claims.

What is claimed is:

1. A system for capturing and processing body measurements comprising:

one or more body scanners, each body scanner configured to capture a plurality of depth images of a user;

a backend system, coupled to each body scanner, configured to receive the plurality of depth images, generate a three dimensional avatar of the user based on the plurality of depth images, and generate body measurement data of the user based on the avatar;

a repository in communication with the backend system configured to associate the body measurement data with the user and store the body measurement data; and an interface configured to retrieve the body measurement data for the user, receive an input for a body measurement, and display an avatar based on the body measurement and remaining body measurement data.

2. The system of claim 1, wherein each body scanner further comprises a platform on which the user is positioned that rotates relative to one or more stationary cameras to capture a body scan comprising the plurality of depth images.

3. The system of claim 1, wherein each body scanner further comprises a stationary platform on which the user is positioned and one or more cameras that each rotate relative to the platform to capture a body scan comprising the plurality of depth images.

4. The system of claim 1, wherein said backend system is further configured to associate a body scanner capture time with the body measurement data.

5. The system of claim 4, further comprising an interface configured to retrieve and display a plurality of three dimensional avatars of different body scanner capture times associated with the user.

6. The system of claim 4, further comprising an interface configured to retrieve and display user body measurement data of different body scanner capture times associated with the user.

7. The system of claim 1, wherein said first interface is further configured to display the avatar based on the retrieved body measurement data, and said input comprises visual indicia overlaying landmarks for body measurements, wherein the visual indicia can be manipulated to input the body measurement and display the avatar based on manipulation of the body measurements and remaining body measurement data.

8. A system for capturing and processing body measurements comprising:

one or more body scanners, each body scanner configured to capture a plurality of depth images of a user;

a backend system, coupled to each body scanner, configured to receive the plurality of depth images, generate a three dimensional avatar of the user based on the plurality of depth images, and generate body measurement data of the user based on the avatar, wherein said backend system is further configured to associate a body scanner capture time with the body measurement data;

a repository in communication with the backend system configured to associate the body measurement data with the user and store the body measurement data;

a first interface configured to retrieve the body measurement data for the user, receive an input for a body measurement, and display an avatar based on the body measurement and remaining body measurement data; and a second interface configured to retrieve user body measurement data from at least one selected body scanner capture time and to project future user body measurement data.

9. The system of claim 8, wherein said first interface is further configured to display the avatar based on the projected user body measurement data.

10. A method for capturing and processing body measurement data comprising:

capturing a plurality of depth images of a user using a body scanners;

providing a backend system coupled to the body scanner and receiving the plurality of depth images, wherein said backend system associates a body scanner capture time with the body measurement data;

generating a three dimensional avatar of the user based on the plurality of depth images;

extracting the body measurement data of the user based on the avatar;

associating the body measurement data with the user and storing the body measurement data in a repository in communication with the backend system; and displaying an interface configured to retrieve and display a plurality of three dimensional avatars associated with the user and different body scanner capture times.

11. The method of claim 10, wherein the body scanner further comprises a platform on which the user is positioned, the method further comprising rotating the platform relative to one or more stationary cameras to capture a body scan comprising the plurality of depth images.

12. The method of claim 10, wherein the body scanner further comprises a platform on which the user is positioned, the method further comprising rotating one or more cameras of the body scanner relative to the platform to capture a body scan comprising the plurality of depth images.

13. The method of claim 10, further comprising displaying an interface configured to retrieve user the body measurement data associated with the user, receive an input for a body measurement, and display the avatar based on the input body measurement and remaining body measurement data.

14. The method of claim 13, wherein said interface is configured to display the avatar based on the retrieved body measurement data, and said input comprises visual indicia overlaying landmarks, each landmark associated with a body measurement, wherein the visual indicia can be manipulated, wherein the interface displays an updated avatar based on manipulation of the body measurement and the remaining body measurement data.

15. A method for capturing and processing body measurement data comprising:

capturing a plurality of depth images of a user using a body scanner;

providing a backend system coupled to the body scanner and receiving the plurality of depth images, wherein said backend system associates a body scanner capture time with the body measurement data;

generating a three dimensional avatar of the user based on the plurality of depth images;

extracting the body measurement data of the user based on the avatar;

associating the body measurement data with the user and storing the body measurement data in a repository in communication with the backend system; and displaying an interface configured to retrieve and display user body measurement data associated with the user and different body scanner capture times.

16. The method of claim 15, further comprising displaying an interface configured to retrieve user body measurement data associated with the user from at least one selected body scanner capture time and projecting future user body measurement data.

17. The method of claim 16, wherein said interface is configured to display the avatar based on the projected user body measurement data.

* * * * *

UNITED STATES PATENT AND TRADEMARK OFFICE
CERTIFICATE OF CORRECTION

| | | |
|---|---|---|
| PATENT NO. | : 9,526,442 B2 | Page 1 of 1 |
| APPLICATION NO. | : 14/269134 | |
| DATED | : December 27, 2016 | |
| INVENTOR(S) | : Gregory A. Moore, Tyler H. Carter and Timothy M. Driedger | |

It is certified that error appears in the above-identified patent and that said Letters Patent is hereby corrected as shown below:

In the Claims

Fourth Line of Claim 10 in the printed patent, the plural "scanners" should be changed to the singular form, "scanner".

Signed and Sealed this
Twenty-fifth Day of April, 2017

Michelle K. Lee
*Director of the United States Patent and Trademark Office*